Figure 1:
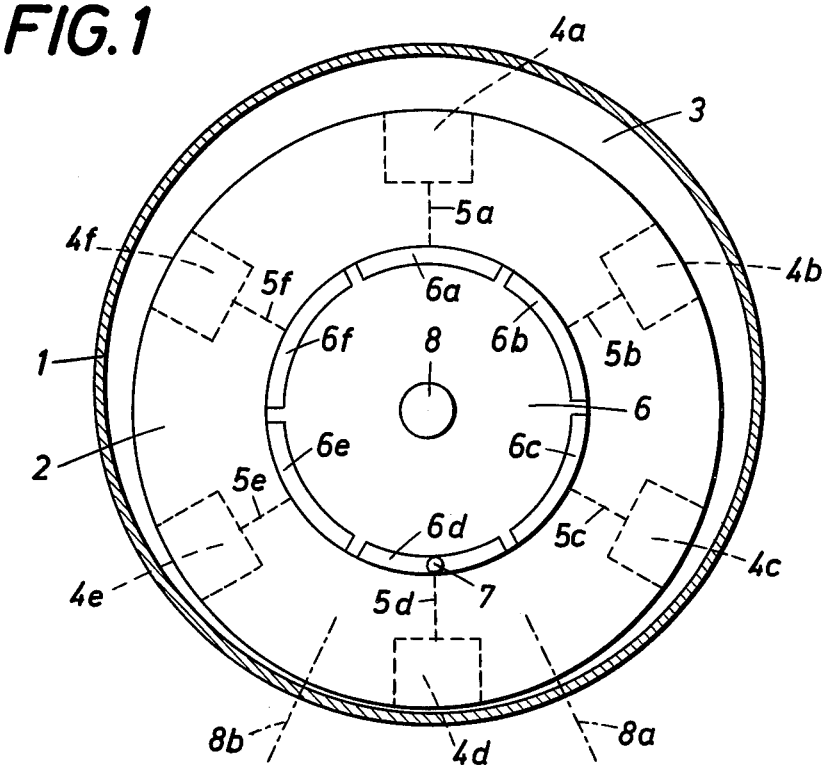

United States Patent [19]

Kretz

[11] 4,102,204
[45] Jul. 25, 1978

[54] ULTRASONIC SECTION PLANE EXAMINATION AND DISPLAY

[76] Inventor: Carl Kretz, Redl 20, Zipf, Austria

[21] Appl. No.: 749,539

[22] Filed: Dec. 10, 1976

[30] Foreign Application Priority Data

Dec. 23, 1975 [AT] Austria .................................. 9777/75

[51] Int. Cl.² ............................................ G01N 29/04
[52] U.S. Cl. ....................... 73/626; 73/639; 73/641; 73/644
[58] Field of Search ............ 73/67.8 S, 67.9, 71.5 US; 340/1 R, 5 MP

[56] References Cited

U.S. PATENT DOCUMENTS

| | | | |
|---|---|---|---|
| 3,415,111 | 12/1968 | Chattaway et al. | 73/67.8 S |
| 3,423,991 | 1/1969 | Collins | 73/67.5 R |
| 3,631,714 | 1/1972 | Cressman | 73/71.5 US |
| 3,714,817 | 2/1973 | Miller | 73/71.5 US |
| 3,817,089 | 6/1974 | Eggleton et al. | 73/67.8 S |
| 3,955,561 | 5/1976 | Eggleton | 73/67.8 S |

FOREIGN PATENT DOCUMENTS 1,121,523  7/1968  United Kingdom ........... 73/71.5 US

*Primary Examiner*—Richard C. Queisser
*Assistant Examiner*—John P. Beauchamp
*Attorney, Agent, or Firm*—Kurt Kelman

[57] ABSTRACT

Moving section plane pictures of a specimen are produced by contacting a predetermined peripheral portion of an ultrasonic transducer head with the specimen in the section plane. The transducer head has a circular internal cavity in which a wheel is mounted eccentrically for rotation about an axis. A plurality of ultrasonic transducers are mounted peripherally on the wheel. The gap formed between a transducer and the internal surface of the transducer head is a minimum along the peripheral portion where contact to the specimen occurs. Each transducer is energized only when passing through the sector subtended by the peripheral portion in contact with the specimen and echoes received by the transducer are displayed on a screen whose base line is synchronized to the movement of the ultrasonic beam. The transducers can be divided into two sets alternately spaced around the wheel, each transducer of one set having a predetermined characteristic differing from the corresponding characteristic of the transducers of the second set. Depending upon the application, transducers of one or the other set are energized selectively or time averages may be obtained by alternate energization of the two sets.

24 Claims, 8 Drawing Figures

FIG.5
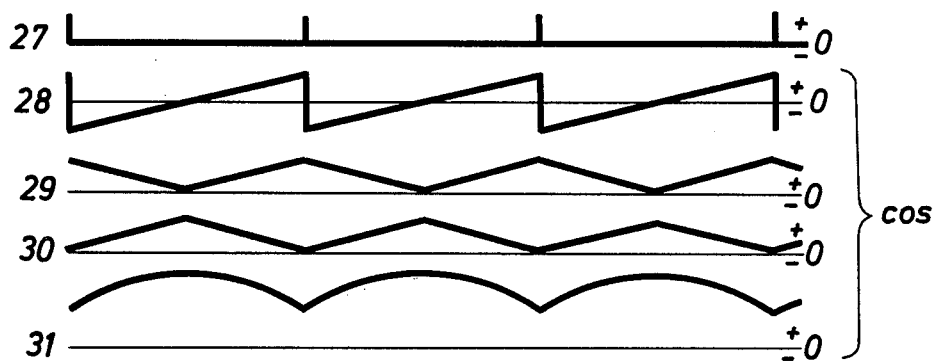
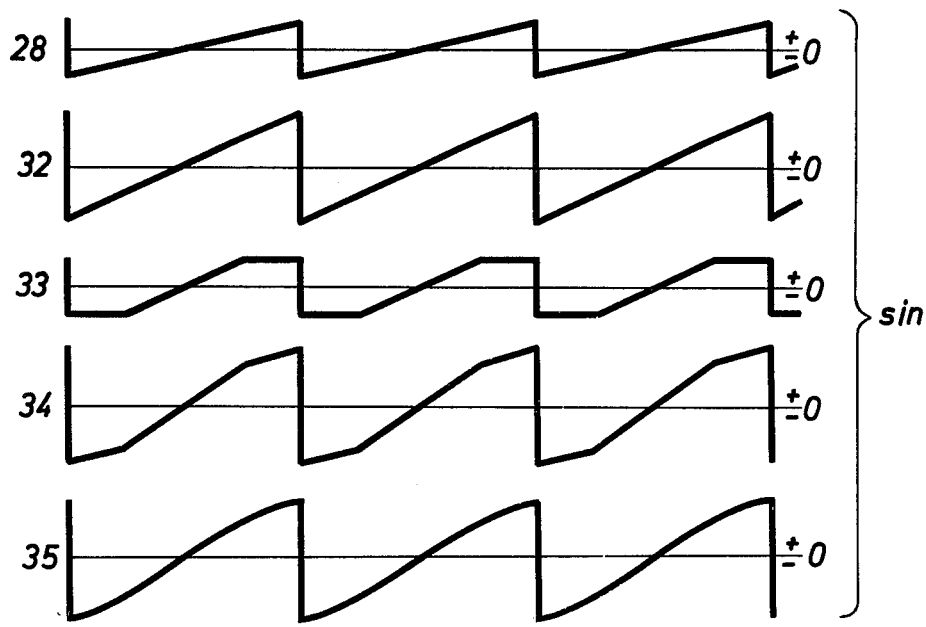
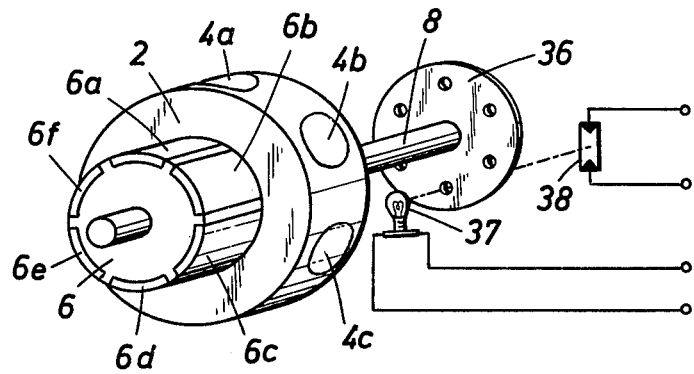
FIG.6

ULTRASONIC SECTION PLANE EXAMINATION AND DISPLAY

This invention relates to a method of producing moving section plane pictures of specimens in response to ultrasonic section plane examination, in which a transducer head is applied to the specimen and a sound beam projected from the transducer head enters the specimen substantially without refraction and without delay or with a delay by a delay line which is negligibly small, of an order of one wavelength or part thereof, said beam is angularly moved in the selected sectional plane, echoes are received and on a fluorescent screen, on which a baseline is moved substantially in synchronism with the sound beam, are displayed at locations which are associated with respective locations at which the echoes have originated.

The invention relates also to an equipment for carrying out that method, comprising a sound transducer head, which is applicable to the specimen and adapted to project a sound beam, which is adapted to enter the specimen and to be angularly moved therein, and an ultrasonic control and display unit for receiving the echoes, said unit comprising a fluorescent screen on which a baseline is angularly moved in synchronism with the sound beam and on which the echoes can be displayed at locations which are associated with the locations at which they have originated.

A slowly scanning display unit in which echo signals which have been received are temporarily stored cannot be employed in the production of moving section plane pictures in response to ultrasonic section plane examination. For that purpose, there must be no storage of pictures and a high frame frequency of an order of about 20 Hz must be employed. So far, these requirements were fulfilled only with equipment which has other serious disadvantages and in which, above all, the picture quality is poorer in every respect than with equipment comprising a slowly scanning display unit for producing still images. The main disadvantages relate to the picture area which can be displayed, the resolution, and the accuracy of the reproduction.

In known equipment of the kind concerned here, an angular movement is imparted to the sound beam in that the transducer head is applied to the specimen to be examined and is pivotally oscillated about an axis which lies approximately in the interfacial plane and in the forward face of the transducer head. Special drive means are provided for this purpose. Whereas the required frame frequency can be achieved with such equipment, only a triangular area in the section plane is examined so that the pictures which are displayed have only very small transverse dimensions in the area which is near the transducer head. Because the sound beams are much closer together near the transducer head, the resolution and the accuracy of the reproduction are much higher in that area than in the area which is remote from the transducer head. When the above-mentioned equipment is to be used to provide more information about the regions which lie closely below the surface of the specimen under examination, the transducer head must be successively applied to different portions and section plane pictures must be made. This practice involves the difficulties that the examination takes a long time, that it is difficult clearly to coordinate the successively produced component section plane pictures, and that always the same pictures or zones are displayed for those regions which are remote from the transducer head.

An effort to eliminate the above-mentioned difficulties has resulted in an arrangement which is disclosed in U.S. Patent Specification No. 3,439,530, and comprises a plurality of sound transducer heads, which can be focused to a common section plane and are adapted to be driven to perform individual angular movements. E.g., for an examination of a skull, these transducer heads can be applied simultaneously to different portions of the periphery of the skull. Whereas the section plane pictures produced with the aid of these transducer heads are also triangular, they do enable a better synopsis. The arrangement has the disadvantage that the positions of the transducer heads relative to each other are usually taken into account in the focusing of the equipment so that the multiple lines are not displayed in the areas in which the individual section plane pictures overlap.

An effort to eliminate the need for such readjustment for each individual examination has resulted in equipment which has been disclosed in Opened German Specification No. 2,329,387 and which also comprises sound transducer heads used in the formation of triangular individual section plane pictures of a common section plane. These transducer heads are arranged on the shell of an immersion tank, in which the specimen to be examined is immersed, and are adapted to be driven so as to perform an angular movement. That equipment has the disadvantage that substantial delay lines through the liquid are disposed between the individual transducer heads and the specimen under examination and ghost echoes can be avoided only if the delay lines have a length in excess of the depth in which the penetration of each sound beam into the specimen is utilized so that the overall depth of penetration and the frame frequency are highly restricted.

Opened German Specification No. 2,215,001 describes equipment which comprises a directly applied multiple sound transducer head that includes a multiplicity of sound transducer systems, which are arranged in a row and by an electronic sequence switch are connected to and disconnected from the control and display unit in rapid succession. That arrangement involves relatively large steps from one transducer system to the next because these systems cannot be made as small as desired. If the size of the vibrator is below a lower limit, the beam spread angle increases and with a size at and below said lower limit the projection of the sound beam in a definite direction is no longer ensured although this is required for the production of a section plane picture. For these reasons the specimen is scanned in a coarse, stationary pattern so that only substantial reflecting surfaces which can be detected by two adjacent systems can be detectably displayed. Smaller reflecting surfaces are liable to be overlooked, particularly if they are sporadic.

Equipment which differs from the type concerned here, in which a sound transducer head is directly applied and projects a sound beam directly into the specimen, has been disclosed, e.g., in Printed German Application No. 1,289,617 and includes a sound transducer head which is rotatable about an axis and carries two or more ultrasonic transducer systems, which are activated as they move along a path that is remote from the specimen and then project a sound beam which first impinges on a parabolic reflector and is reflected thereby into the specimen. Because the transducer head is disposed at the focus of the parabolic reflector, the sound beams which are reflected when the transducer head is in different angular positions are parallel to each other. As a result, a rectangular sectional area of the specimen can be scanned with sound beams which are parallel to each other.

To enable an examination of the specimen from different aspects without a removal of the transducer head, the latter may be provided with sound transducer systems which have different characteristics, e.g., different frequencies, and are arranged in alternation and only transducer systems of the same kind are connected to the control and display unit during one examinination. Such equipment has been described in Austrian Patent Specification No. 316,737.

As has already been explained in connection with the design disclosed in Opened German Specification No. 2,329,387 a travel of the sound waves along a long delay line in the sound-optical system inherently results in a disadvantage. To prevent a generation of repeated echoes in the reflecting system, the sound path in the sound-optical system must be longer than the sound path in the specimen to be examined. This results in a loss of more than one-half of the length of the sound path which is available and the sound beam can penetrate the specimen only to a small depth. The entire sound path consisting of the delay line and the penetrating path is long and results in long transit times for the sound pulses and echoes. For this reason, the pulse rate must be low and the frame frequency must be low too so that a coarse scanning pattern results and the picture is not free from flicker. The frame frequency cannot be increased by an increase of the angular velocity because this would result in a coarser scanning pattern and in a lower lateral resolution. The axis of the transducer head must be oblique to the focal line of the reflector, or each transducer system must project a beam in a somewhat oblique direction because otherwise the reflected sound beam would impinge on the transducer head rather than enter the specimen.

It is an object of the invention to provide a method and equipment for producing moving section plane pictures at a sufficiently high frame frequency and with a useful frame configuration, a high resolution and a high sensitivity, whereas long delay lines for the sound beam are avoided and a moving sound generator is satisfactorily coupled to the specimen.

In the method according to the invention this object is accomplished in that the sound beam is produced by a plurality of ultrasonic transducer systems, which revolve around a common axis, which is outwardly spaced apart from the specimen, each of these systems is connected to a control and display unit only during the movement of that system in a sector which is associated with the specimen and each of these systems is activated during its movement over the surface of the specimen so that the sound beam scans the section plane in a basically trapezoidal area which adjoins the activated system, and the base line of the section plane picture is analogously moved over a substantially trapezoidal area of the fluorescent screen.

Equipment according to the invention is characterized in that the transducer head comprises a plurality of ultrasonic transducer systems, which revolve around a common axis, which is outwardly spaced from the specimen, each of these transducer systems is connected to a control and display unit only during the movement of that system in a sector which is associated with the specimen, each of these systems is adapted to be activated during its movement over the surface of the specimen so that the sound beam scans the section plane in a basically trapezoidal area which adjoins the activated system, and the base line of the section plane picture produced by the display unit is also adjustable over a substantially trapezoidal area of the fluorescent screen.

In accordance with the invention, a rotating transducer head is also employed but in contradistinction to known equipment and methods the sound beam is virtually directly projected into the specimen. This is of decisive advantage, as has been mentioned. Because the sound beam is movable over a trapezoidal area in the section plane, the ideal theoretical condition, under which a rectangular area is scanned by a sound beam that is moved parallel to itself, can be substantially approximated. In comparison to the use of a transducer head which is angularly movable about an axis which extends through the coupling interface and scans a triangular area in the section plane, the practice of the invention results in a section plane picture which exhibits a much lower variation in its lateral resolution and in its sensitivity in zones at different depths. Whereas the known directly coupled system is carried by an angularly oscillating sound transducer head, the present sound transducer head rotates in a uniform direction and for that reason can be driven by simple means.

In an embodiment of equipment according to the invention, the sound transducer head comprises a stationary housing and a known wheel, which is mounted in said housing and adapted to be driven to rotate and carries separate sound transducer systems, each of which is adapted to be connected to the control and display unit by a switch only during the movement of that system through a predetermined sector, the wheel and housing are coupled by a sound-conducting liquid, and the deflection of the base line of the display unit is synchronized with the rotation of the wheel of the sound transducer head as successive sound transducer systems move through the field-defining sector, which is disposed between the axis of rotation and the specimen and defines the shorter parallel side of the substantially trapezoidal section plane picture, and, at least adjacent to the field-defining sector, the gap which exists between the housing of the sound transducer head and the wheel and which is filled with sound-conducting liquid is small and preferably smaller than one-half of the wavelength of the ultrasonic waves in the liquid.

If the wheel of the transducer head is eccentrically disposed in an associated circular cavity defined by the housing of the transducer head, the gap left between the wheel and the periphery of the cavity will have the smallest width in the field-defining sector.

The housing of the transducer head may consist at least in the field-defining sector of a material which has at least approximately the same acoustic resistance as the coupling liquid.

If the transducer systems mounted on the wheel of the transducer head are uniformly spaced in the peripheral directions, the angular spacing of adjacent transducer systems may be approximately as large as the angular width of the field-defining sector in the direction of movement.

According to a further feature, transducer systems having different properties, e.g., different diameters, different acoustic lenses are carried in alternation by the wheel of the transducer head, and a preselector switch is provided to select a set of similar systems for connection to the control and display unit by the sequence switches.

The wheel may carry a plurality of contact members, which are separated by insulating strips and associated with respective transducer systems and adapted to cooperate with a wiping contact so that all these contact members together form virtually a commutator. In that case the control and display unit is connected to a given transducer system as long as the associated contact member contacts the wiping contact. By means of these contact members, the signals which initiate the generation of the pulses to be projected are transmitted to the respective transducer system and the signals derived from the received echo pulses are transmitted from said system to the control and display unit.

In accordance with a further feature, the transducer systems are coupled to the control and display unit by means of an impedance-matching element, preferably a transformer, which has two coaxial windings, one of which rotates with the wheel whereas the other is stationary, and the wheel contains preferably a plurality of switches, which are forcibly controlled from the outside and associated with respective transducer systems.

In such arrangement, the signals can be transmitted without need for a direct d.c. connection. The windings of the transformer are so designed that they exert the same influences on each other whether or not one of them is rotating. As a result, only a change of the current flowing in one winding can induce a voltage in another winding. Known means for preventing a distortion of the signals or for a correction of distorted signals may also be provided. Where a plurality of transducer head wheels are provided which may be used in connection with the same section plane picture display unit, the windings connected to the wheels will be identical, at least in diameter, and be designed to fit into the stationary winding so that the winding connected to each wheel can be exchanged together with the wheel. Alternatively, the winding to be connected to the wheel may be permanently mounted in the other winding and be releasably connected to the wheel during operation by means which are provided for this purpose.

According to a preferred feature, the switches are contactless and actuated by a magnetic field.

Where the wheel carried transducer systems having different properties and arranged in alternation, a separate impedance-matching element may be associated with each set of systems having the same properties or, in another embodiment, a selection of each set having similar properties can be enabled in that the switches rotating with the wheel and the means for actuating these switches are spaced apart by center distances which are different but are the same for each set of transducer systems having the same properties. In the latter case, each set of transducer systems can be selected for a given examination in that the stationary stops which cooperate with the actuating means are adjusted to lie on certain diameters of the wheel.

Figure 2:
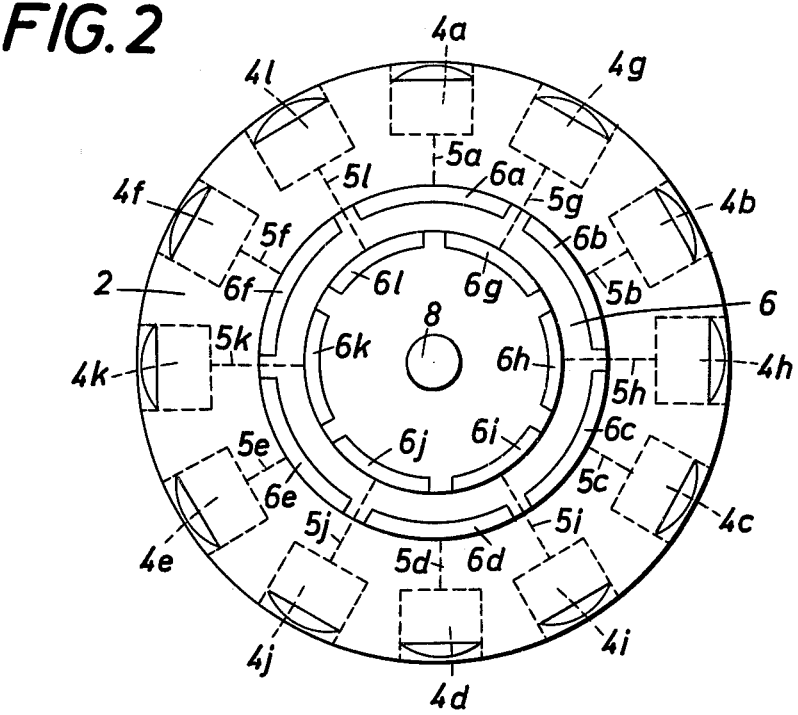
Figure 3:
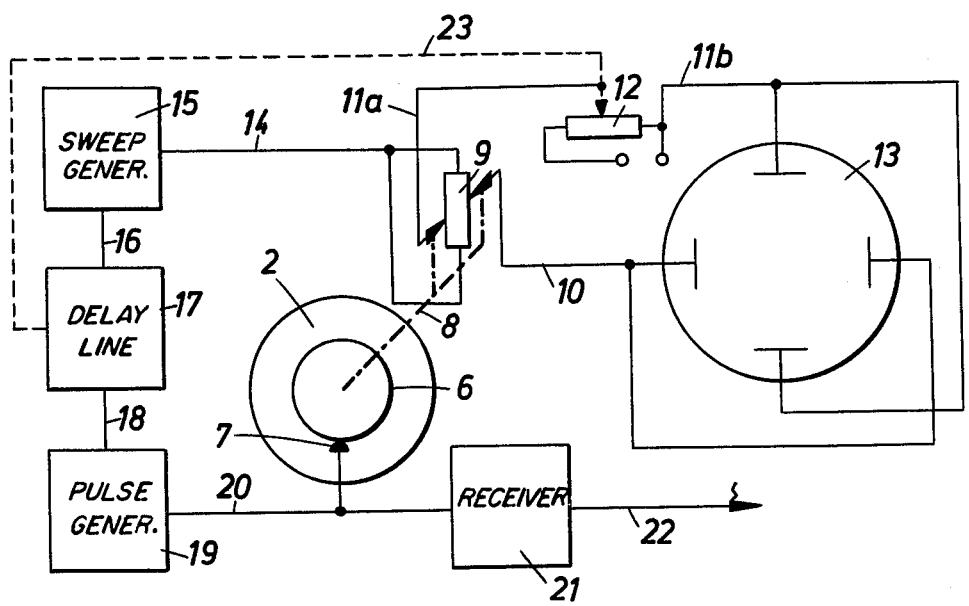
Figure 4:
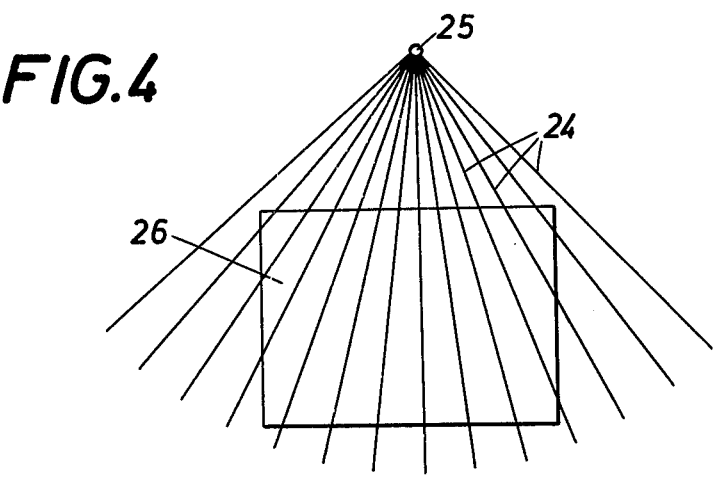
Figure 7:
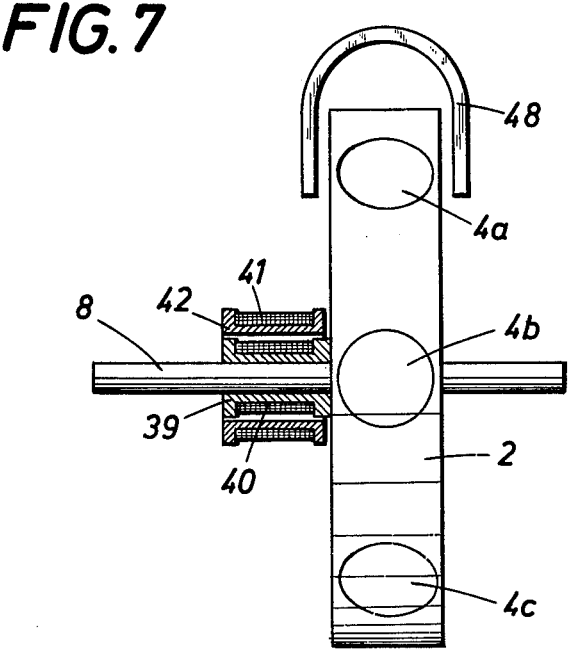
Figure 8:
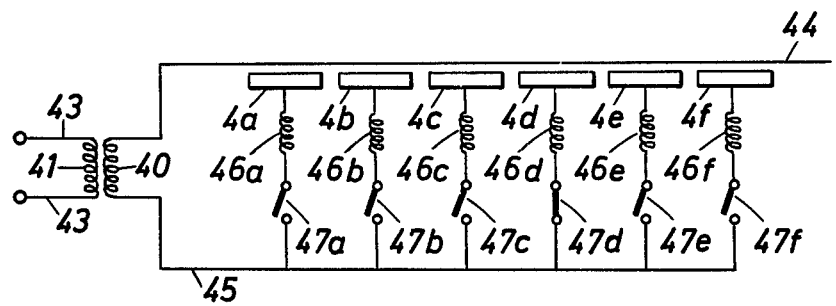

Further details and advantages of the subject matter of the invention will become apparent from the following description of the accompanying drawings, in which FIG. 1 is a diagrammatic view showing the basic arrangement of a sound transducer head which can be used in the method and equipment according to the invention, FIG. 2 is a view which is similar to FIG. 1 and shows details of a wheel used in a sound transducer head, FIG. 3 is a block circuit diagram of equipment according to the invention, FIG. 4 a sketch explaining the scanning pattern, FIG. 5 a diagrammatic representation showing how a certain control voltage to be applied to the deflecting plates of a picture tube can be derived from a sweep voltage in the method according to the invention, FIG. 6 a diagrammatic representation showing the generation of control pulses in synchronism with the movement of a sound transducer system through a field-defining sector, FIG. 7 a diagrammatic elevation showing another wheel for use in a sound transducer head, and FIG. 8 an associated circuit diagram.

In accordance with FIG. 1, a sound transducer head comprises a housing 1 and a wheel 2 rotatably mounted in the housing. A gap 3 between the wheel and housing is filled with a sound-transmitting liquid. Sound transducer systems $4a$ to $4f$ are carried by the wheel 2 at its periphery and are regularly spaced apart and electrically disconnected from each other at least with respect to one terminal. Each sound transducer system is connected by one of the separate leads $5a$ to $5f$ to one of the segments $6a$ to $6f$, which are insulated from each other and constitute a slip ring, which cooperates with a pick-up 7, which is constituted by a wiper contact 7. In practice, contactless (e.g. inductive) pick-up may be used alternatively. During a rotation of the wheel 2 in the clockwise sense, the several transducer systems $4a$ to $4f$ are successively connected to a control and display unit. This is shown in FIG. 1 for the transducer system $4d$, which is in a field-defining sector that is limited by boundary lines $8a$ and $8b$. During the movement of a transducer system through that sector, the transducer system is activated by the control and display unit to project sound pulses at a certain frequency and is adapted to receive the resulting echoes from the specimen. Adjacent to the field-defining sector, the housing 1 is coupled to the specimen.

If the wheel of the transducer head would carry only one sound transducer system, the required frame frequency of 20 frames per second could be achieved only if the wheel performed 20 revolutions per second. Whereas in that arrangement a trapezoidal area would be scanned rather than a less desirable triangular area and the transducer head would perform a uniform motion rather than an oscillatory one, some disadvantages would still be present. The periphery of a wheel rotating at the required speed moves at a considerable velocity, at which it may be difficult to project the sound waves. Besides, the arrangement would still result in a coarse scanning of the area to be displayed. At an assumed pulse rate of 6000 Hz, the transducer head would rotate through 1.2° between two sound pulses projected in direct succession so that the scanning pattern would be relatively coarse in more remote regions of the areas to be displayed. A low efficiency would also result because with a field-defining sector subtending an angle of 60° the interval between the completion of one section plane picture and the beginning of the tracing of the next section plane picture would be five times the interval required to trace a single frame. These unfavorable conditions can be eliminated immediately if, as is shown on the drawing, the wheel of the transducer head carries a plurality of sound transducer systems, which are regularly spaced. For the same frame frequency, the speed can now be decreased in inverse proportion with the number of transducer systems which are employed so that the density of the scanning pattern is proportionally increased. In the embodiment shown on the drawing, a speed of only 3.33 revolutions per second would be sufficient and the angular movement of the transducer systems between two successive pulses would be only 0.2°. This means a substantially continuous scanning because the sound beam has a finite width so that the several beams virtually adjoin each other. If, in addition, the angular spacing of two adjacent transducer systems is equal to the angle subtended by the field-defining sector, there will be no interval between two successive section plane pictures because the completion of each picture will immediately be succeeded by the tracing of the next following picture, and a high efficiency will be obtained also in this respect. This requirement is desirably fulfilled although this is not essential.

The sound to be projected travels from the protective layer on the face of the projecting one of the transducer systems 4a to 4f through the liquid layer disposed in the gap 3 between the transducer system and the housing wall 1 and then through the latter before the sound enters the specimen under examination. Whereas the resulting loss is negligibly small relative to the total sound path length which can be utilized, the width of the zone which directly adjoins the transducer head and which cannot be examined is increased. That dead zone is mainly determined by the width of the projected pulse and in the present case also by multiple reflexions, which occur mainly in the liquid layer and in most cases cannot be separated from the projected pulse and for this reason result in a virtual widening of that pulse. It has been found that these difficulties can be substantially eliminated by the following measures: When the liquid-filled gap is very small, the several reflexions succeed each other so closely that the total time in which they occur is shorter than with a wider gap. Particularly desirable conditions will be obtained if the width of the liquid-filled gap is smaller than one-half of the wavelength of the sound waves which occur. Besides, the number of multiple reflexions which occur may be greatly reduced in that the acoustic resistance of the material of the housing is matched as closely as possible to the acoustic resistance of the liquid. As a result, only a very small portion of the energy is reflected in each reflexion and a major portion is transmitted outwardly through the housing wall. In an ideal case, when the housing wall and the liquid have the same acoustic resistance, there will be no reflexion at all.

In accordance with FIG. 1 the wheel 2 of the transducer head is eccentric with respect to the cavity 3 of the housing. Whereas this arrangement is not essential, it affords various advantages. As has been mentioned, the liquid-filled gap should be minimized in the field-defining sector. The provision of such narrow gap throughout the periphery would require a manufacture with high precision. Because such narrow gap is required only in the field-defining sector, this requirement can be fulfilled more easily and with a smaller expenditure by the eccentric arrangement. This results also in a reduced friction so that a smaller driving power is required. Besides, a larger volume of liquid is available so that any leakage losses will be less significant.

FIG. 2 shows a modified wheel 2 of the transducer head. The main difference does not reside in the fact that the number of transducer systems is larger than in FIG. 1 but in the fact that the transducer systems are combined in two sets, which are connected to different slip rings. Transducer systems 4a to 4f lie on an outer slip ring comprising segments 6a to 6f. Transducer systems 4g to 4l lie on an inner slip ring comprising segments 6g to 6l. One set or the other can be preselected by a simple shifting of the wiping contact. If the systems of the two sets have different properties, e.g., different frequencies, a change between such properties can thus be effected in a simple manner without need for an exchange of the wheel. It will be understood that this concept can be expanded in that more than two sets of systems are mounted in the wheel so that more alternatives are provided. A limit is imposed in this respect only by the size of each system, the space which is available and the desired number of systems in each set.

Alternatively, various properties can be changed during the use of the systems of a set so that the display is based on a time average of the properties of the several systems. It is known, e.g., that the sensitivity of a sound transducer system varies along the axis and has maxima and minima at certain distances, which depend on the ratio between the diameter of the vibrator and the wavelength of the transducer system. If the diameter is changed whereas the frequency remains the same, one sound transducer system may have a maximum sensitivity at a distance at which another transducer system has a minimum sensitivity. If such transducer systems are arranged in alternation in a set, the variation of sensitivity over a substantial time will be farily compensated for a substantial depth range. In that connection, the term "substantial time" must not be interpreted strictly literally because the compensation is effected even by two successive pictures, i.e., in 0.1 second at a frame frequency of 20 Hz.

In the production of the section plane picture, the base line on the fluorescent screen of the control and display unit must perform the same movement as the sound beam in the specimen under examination. FIG. 3 shows how this could be accomplished in a simplified case, in which the wheel of the transducer head carries only one system. By means of a shaft 8 the wheel 2 of the transducer head is connected to the slider of a sine-cosine potentiometer 9. One slider is connected by a line 10 to the plates for horizontally deflecting an electrode beam in a cathode ray tube 13. The second slider is connected by leads 11a and 11b to the vertical deflecting plates. A d.c. voltage can be additionally applied to the plates by means of a potentiometer 12, which is connected between leads 11a and 11b. If a constant d.c. voltage were applied at the potentiometer 9 and no voltage were applied at the potentiometer 12, the electron beam would move at the same frequency of revolution as the wheel 2 of the transducer head and would trace on the fluorescent screen of the cathode ray tube 13 a concentric circle having a radius which represents the voltage applied at the sine-cosine potentiometer 9. On the other hand, if a sweep voltage at a frequency which is much higher than the frequency of revolution of the wheel of the transducer head were applied via a lead 14 to the sine-cosine potentiometer 9, the electron beam would trace on the fluorescent screen a line which originates at the center and revolves in synchronism with the wheel of the transducer head. This line constitutes the base line for the section plane picture. By the d.c. voltage applied via the potentiometer 12, the center of rotation can be vertically shifted even beyond the fluorescent screen. The required sweep voltage is produced by a sweep generator 15 and serves also to initiate the pulses to be projected. Because the beginning of each sweep period is represented by the center of rotation of the base line and the pulses are projected from the sound transducer system (4a to 4l), which are spaced from the center of the wheel 2 of the transducer head, the triggering of each pulse to be projected must be delayed after the beginning of the sweep period for a time which corresponds to the time required by a sound pulse to travel from the center of the wheel to its periphery. To that end, the sweep voltage is applied via a lead 16 to a delay line 17 and from the latter via a lead 18 to a pulse generator 19 to trigger the same. The electric pulse travels via lead 20 and, on the one hand, via the wiper contact 7 and the slip ring 6 to the transducer system which is then operative and, on the other hand, to a receiver 21, to which the echo signals are applied via the same lead. When these signals have been properly processed, they are used via lead 22 for the brightness control of the cathode ray tube. The delay of the pulse to be projected may be controlled via a lead 23 in such a manner that the pulse remains always visible on the fluorescent screen as the picture is displaced.

When only one transducer system is employed, the traced line (base line) always rotates through 360°, like the wheel of the transducer head. A different motion of the base line would be required where a plurality of sound transducer systems are used. That motion is diagrammatically shown in FIG. 4. The base line performs an angular movement about the point 25, which is suitably disposed outside the fluorescent screen. Several successive positions of the base line are represented by lines 24 although the angular spacing between two successive lines is greatly exaggerated. When the base line moving from right to left has performed a certain angular movement and has reached the left-hand edge of the picture, it would have to fly back to its initial position and begin another sweep. This angular movement is equal to the angular movement of the transducer system through the field-defining sector and the flyback corresponds to the switch-over to the next transducer system entering the field-defining sector. This problem could be solved in that a plurality of sine-cosine potentiometers are mounted on the shaft 8 and are associated with respective transducer systems and arranged with the same angular spacing as the latter, and each of these potentiometers could be connected in circuit at the same time as the associated transducer system, e.g., by means of switch contacts controlled by the shaft for the wheel of the transducer head.

Whereas the arrangement which has been described meets the requirements in theory, it is believed that it will not give full satisfaction in practice because mechanically actuated contacts wear rapidly so that trouble could arise. A control which uses no mechanically moved parts would appear to be preferable. A possible embodiment of that concept will now be described.

Whenever a transducer system enters the field-defining sector, a short electric pulse is generated, so that the waveform 27 in FIG. 5 results. These voltage pulses are used to initiate the generation of a sweep voltage, which rises until the next pulse arrives. In response to each pulse, the sweep then in progress is interrupted and a new sweep begins. This results in the voltage waveform 28. This sweep voltage must not be confused with the sweep voltage generated in the sweep generator for tracing the base line, and its frequency is the same as the frame frequency, e.g., 20 Hz. By full-wave rectification, this sweep voltage is converted into a delta voltage 29, which is phase-inverted to produce a phase-opposed voltage 30, which is applied to a function generator and converted therein to a cosine voltage 31, which does not represent the cosine from 0° to 360° but the cosine from $-\alpha$ to $+\alpha$ and then begins again at $+\alpha$, where $\alpha$ designates one-half of the angular movement of a transducer system through the field-defining sector. The sine voltage is also derived from the sweep voltage 28, which is initially amplified to a sweep voltage 32, which is equal in frequency but larger in amplitude. A clipping circuit clips the amplitude peaks of the amplified sweep voltage. The voltages 28 and 33 are then combined to produce the waveform 34, which is a good approximation to a sine function between $-\alpha$ and $+\alpha$. This voltage can be applied to another function generator, the output voltage waveform 35 of which is an even better representation of the sine function between $+\alpha$ and $-\alpha$. If the selected angle is not too large, the sine function in the range from $-\alpha$ to $+\alpha$ can be represented in the voltage waveform by a simple straight line, e.g., by the sweep voltage 28 itself. A simple calculation shows that for an angular range from $-30°$ to $+30°$ the error involved in the use of a simple sweep voltage rather than an exactly sinusoidal voltage is smaller than 2%. The required deflecting voltages are now obtained in that the resulting sine and cosine voltages are modulated with the sweep frequency used to trace the base line.

For a satisfactory function, the trigger pulses must be synchronized with the movement of the wheel of the transducer head. An embodiment of a control system used for this purpose is shown in FIG. 6. The shaft 8 for the wheel 2 of the transducer head carries an apertured disc 36, which in dependence on the rotation of the wheel of the transducer head opens and closes the path of light emitted by an incandescent bulb 37 onto a light detector switch 38 so that the required pulses can easily be generated.

The embodiments which have been described may be modified in numerous details within the basic concept of the invention. For instance, the transducer systems may be connected to the control and display unit by means of inductively coupled coils rather than wiper contacts. Besides, the above-mentioned sensitivity variation of the transducer systems of a set may not only be obtained by the use of systems differing in size but also by the provision of pre-arranged acoustic lenses having different focal lengths. The light-sensitive pulse generator which has been described may be replaced by capacitive or inductive means for producing the required pulses. These and numerous other modifications which can be conceived do not affect the basic concept, which resides in that a plurality of sound transducer systems are mounted at the periphery of a rotating wheel, each system is operated when it moves through a field-defining sector, and a base line traced on a fluorescent screen is deflected in accordance with the movement of the sound beam in the specimen under examination. A modified embodiment which may be adopted will be described with reference to FIGS. 7 and 8.

Again, a shaft 8 carries a wheel 2 of a sound transducer head. A plurality of sound transducer systems 4a to 4f are mounted on said wheel and regularly spaced apart in the peripheral direction. As has been described, the wheel 2 of the sound transducer head is accommodated in a housing.

A coil body 39 is fixed to the shaft 8 to rotate with the wheel 2 and contains a winding 40, which constitutes the secondary winding of a transformer and cooperates with a primary winding 41, which is held in a fixed coil body 42, which is concentric with the coil body 39. Owing to the coaxial arrangement of the coils or windings 40, 41, the rotation will not induce a voltage in coil 40.

The primary winding 41 is connected by leads 43 to the control and display unit. Control pulses supplied via leads 43 are transmitted by the transformer windings 40, 41 to leads 44, 45 disposed in the wheel. Series circuits comprising each of one of the transducer systems 4a to 4f, one of compensating coils 46a to 46f, and one of switches 47a to 47f are connected in parallel between these leads 44, 45. During the movement of each transducer system through the field-defining section, the associated switch, in the condition shown the switch 47d, is forcibly closed by its actuating means so that the transducer system receives the control pulses and converts them into sound pulses, which are projected into the specimen. As long as the transducer system is activated, it receives echoes from the specimen and converts them into electric pulses, which are transmitted to the control and display unit via leads 44, 45, transformer 40, 41, and leads 43 and are subsequently displayed. In the embodiment shown by way of example, the switches are controlled by a permanent magnet 48, which has a magnetic field by which each of the switches 47a to 47f is closed as it moves past the magnet. Adjustable solenoids or mechanically operated switches moved, e.g., past a control cam might be used for the same purpose, if desired.

The compensating coils 46a to 46f serve to compensate any differences between the capacitances of the transducer systems 4a to 4f and will not be required if identical sound transducer systems are employed.

What is claimed is:

1. Equipment for ultrasonic examination of a specimen in a section plane and for producing moving section plane pictures in response to said examination, comprising, in combination, an ultrasonic transducer head having a predetermined peripheral portion, said predetermined peripheral portion having an outside surface adapted to be contacted with said specimen in a predetermined section plane, said ultrasonic transducer head comprising a stationary housing having an internal cavity circular in shape at least throughout the sector subtended by said predetermined peripheral portion, and said ultrasonic transducer head further comprising a wheel mounted in said housing for rotation around an axis spaced inwardly from said peripheral portion and eccentrically thereto, the periphery of said wheel and said internal surface of said stationary housing defining a gap extending around said periphery of said wheel and having the smallest width in said sector; a sound transmitting liquid filling said gap; a plurality of ultrasonic transducer means peripherally spaced around said wheel and adapted to revolve therewith around said axis, for projecting an ultrasonic beam through said peripheral portion into said specimen upon activation thereby causing said beam to perform an angular movement in said predetermined section plane, and for receiving, through said peripheral portion, echoes originating at echo-producing portions of said specimen in said section plane in response to said beam and generating corresponding echo signals; control means for operating each of said transducer means; display means having a fluorescent screen and adapted to be operatively connected to each of said transducer means, for tracing on said screen a base line moving angularly in synchronism with the movement of the ultrasonic beam of a transducer means connected thereto to sweep a substantially trapezoidal area of said screen, and for displaying on said screen echo signals from the transducer means connected thereto at locations representing echo-producing portions of said specimen; and activating means for activating each of said transducer means, said activating means comprising means for operatively connecting each of said transducer means to said control means and to said display means only while said transducer means moves along said predetermined peripheral portion, whereby the thus-activated transducer means projects said beam into said specimen and sweeps a substantially trapezoidal area in said predetermined plane, said substantially trapezoidal area adjoining said thus-activated transducer means.

2. Equipment as set forth in claim 1, wherein said transducer means are uniformly spaced at angles substantially equal to the angle subtended by said predetermined peripheral portion.

3. Equipment as set forth in claim 1, wherein said stationary housing has a circular internal cavity; and wherein said wheel is mounted in said circular internal cavity.

4. Equipment as set forth in claim 3, wherein said activating means comprises a plurality of switching means mounted on said wheel for rotation therewith and electrically coupled to corresponding ones of said transducer means for activating each of said corresponding transducer means only during its movement through the sector subtended by said predetermined peripheral portion.

5. Equipment as set forth in claim 1, wherein said smallest width of said gap is less than one-half the wavelength of said beam in said liquid.

6. Equipment as set forth in claim 1, further comprising a delay line for transmitting said beam from said thus activated transducer means into said specimen, said delay line having a length which is smaller than the wavelength of said beam in said delay line.

7. Equipment as set forth in claim 1, wherein said predetermined portion of said housing has approximately the same acoustic resistance as said sound-transmitting liquid.

8. Equipment as set forth in claim 1, wherein said activating means further comprise impedance-matching means arranged to be electrically coupled between said control means and said display means, on the one hand, and each of said transducer means when thus activated, on the other hand.

9. Equipment as set forth in claim 8, in which said impedance-matching means comprise
   a first transformer winding centered on said axis, arranged to revolve in unison with said transducer means and arranged to be electrically coupled to each of said transducer means when it is thus activated, and
   a stationary second transformer winding centered on said axis, inductively coupled to said first winding and electrically coupled to said control means and said display means.

10. Equipment as set forth in claim 9, in which said activating means further comprise a plurality of switches, each associated with one of said transducer means and arranged to electrically couple said transducer means to said first winding only when said transducer system moves through said sector.

11. Equipment as set forth in claim 10, in which said activating means further comprise actuating means for forcibly actuating each of said switches when the transducer means associated therewith moves through said sector.

12. Equipment as set forth in claim 11, in which
each of said switches is adapted to be actuated in response to a magnetic field and
said actuating means are adapted to produce a magnetic field for actuating each of said switches.

13. Equipment as set forth in claim 7 wherein said display means comprise
two pairs of deflecting plates and
deflecting voltage-generating means for periodically applying to one of said pairs of deflecting plates a deflecting voltage in synchronism with the movement of successive ones of said transducer means through said sector,
said deflecting voltage having a waveform approximating a sine-cosine function in the angular range subtended by said sector.

14. Equipment as set forth in claim 13, in which
said transducer means have a uniform angular spacing,
said drive means are operable to move successive ones of said transducer means through said sector at a predetermined frequency and
said deflecting voltage-generating means are operable to apply said deflecting voltage to said one pair of deflecting plates at said frequency.

15. Equipment as set forth in claim 1, wherein said display means further comprises means responsive to a synchronizing pulse, for furnishing a sine-cosine deflecting voltage, and pulse generator means for furnishing said synchronizing pulse to said means for furnishing a sine-cosine deflecting voltage whenever one of said transducer means enters said sector.

16. Equipment as set forth in claim 15, wherein said pulse generator means comprises a disc arranged to revolve about said axis in synchronism with said transducer means.

17. Equipment as set forth in claim 16, wherein said disc has a plurality of apertures, each associated with one of said transducer means; and wherein said pulse generator means further comprises a light source and light detector means disposed on opposite sides of said disc and positioned relative to said transducer means in such a manner that light from said light source falls on said light detector means through one of said apertures whenever one of said transducer means enters said sector, said light detector means comprising means for furnishing said synchronizing pulse to said means for furnishing said sine-cosine deflecting voltage in response to light received from said light source.

18. Equipment for ultrasonic examination of a specimen in a section plane and for producing moving section plane pictures in response to said examination, comprising, in combination, an ultrasonic transducer head having a predetermined peripheral portion the outside surface of said predetermined peripheral portion being adapted for contact with a specimen in a predetermined section plane; a plurality of peripherally spaced ultrasonic transducer means mounted in said transducer head and adapted to revolve in said predetermined plane around a common axis spaced inwardly from said peripheral portion, each for projecting an ultrasonic beam through said peripheral portion into said specimen when contacting said specimen in said predetermined plane, thereby causing said beam to perform an angular movement in said predetermined plane, and for receiving, through said peripheral portion, echoes originating at echo producing portions of said specimen in said section plane in response to said beam and generating corresponding echo signals, said plurality of transducer means comprising a first and second set of transducer means, each of said transducer means in said first set having a predetermined characteristic differing from the corresponding predetermined characteristic of the transducer means in said second set, the transducer means of said first and second sets being arranged in alternation in said transducer head; control means for operating each of said transducer means; display means having a fluorescent screen and adapted to be operatively connected to each of said transducer means, for tracing on said screen a base line moving angularly in synchronism with the ultrasonic beam of a transducer means connected thereto to sweep a substantially trapezoidal area on said screen, and for displaying on said screen echo signals from the transducer means connected thereto at locations representing echo-producing portions of said specimen: and activating means for activating each of said transducer means, said activating means comprising selector switch means operable to select said first or said second set of transducer means, thereby furnishing a selected set of selected transducer means, said activating means further comprising means for operatively connecting each of said selected transducer means to said control means and to said display means only while said selected transducer means moves through the sector subtended by said predetermined peripheral portion of said transducer head.

19. Equipment as set forth in claim 18, wherein each of said transducing means comprising a lens; and wherein said predetermined characteristic wherein transducing means of said first set differ from transducing means of said second set is the diameter of said lens.

20. Equipment as set forth in claim 18, wherein each of said transducing means comprises a lens; and wherein said predetermined characteristic wherein transducing means of said first set differ from transducing means of said second set is the focal length of said lenses.

21. Equipment as set forth in claim 18, wherein said predetermined characteristic is the operating frequency, of said transducing means.

22. Equipment as set forth in claim 18, wherein said transducing means of said first set having a maximum sensitivity at a first predetermined distance from said transducing means and said transducing means of said second set have a maximum sensitivity at a second predetermined distance from said transducing means, said second predetermined distance differing from said first predetermined distance.

23. Equipment as set forth in claim 18, wherein said activating means further comprises a plurality of sets of switching means arranged to revolve in unison with said transducer means, the switching means of each of said sets are electrically coupled to respectively associated transducer means of one of said sets and arranged to activate each of said associated transducer means only during its movement along said predetermined peripheral portion, and said switching means of each of said sets have a uniform angular spacing, which differs from the angular spacing of the switching means of the others of said sets.

24. Equipment as set forth in claim 18, wherein said activating means comprise a plurality of impedance-matching means, each associated with one of said sets of transducer means and arranged to be electrically coupled between said control means and said display means, on the one hand, and each of the transducer means of the associated set when said transducer means is activated, on the other hand.

* * * * *